(12) United States Patent
Lintner

(10) Patent No.: US 7,998,493 B2
(45) Date of Patent: Aug. 16, 2011

(54) COSMETIC OR DERMOPHARMACEUTICAL COMPOSITIONS WHICH ARE USED TO REDUCE BAGS AND CIRCLES UNDER THE EYES

(75) Inventor: Karl Lintner, Paris (FR)

(73) Assignee: Sederma SAS (FR)

( * ) Notice: Subject to any disclaimer, the term of this patent is extended or adjusted under 35 U.S.C. 154(b) by 1634 days.

(21) Appl. No.: 10/504,643

(22) PCT Filed: Feb. 10, 2003

(86) PCT No.: PCT/FR03/00441
§ 371 (c)(1),
(2), (4) Date: Feb. 25, 2005

(87) PCT Pub. No.: WO03/068141
PCT Pub. Date: Aug. 21, 2003

(65) Prior Publication Data
US 2005/0142092 A1 Jun. 30, 2005

(30) Foreign Application Priority Data

Feb. 15, 2002 (FR) .................................... 02 01967

(51) Int. Cl.
*A61K 6/00* (2006.01)
(52) U.S. Cl. ........... 424/401; 424/78; 424/400; 424/725
(58) Field of Classification Search .................. None
See application file for complete search history.

(56) References Cited

U.S. PATENT DOCUMENTS

| | | | |
|---|---|---|---|
| 3,578,719 A | 5/1971 | Kalopissis | |
| 3,821,372 A | 6/1974 | Vanlerberghe et al. | |
| 4,666,711 A | 5/1987 | Vanlerberghe et al. | |
| 5,627,157 A * | 5/1997 | Hijiya et al. ............... | 514/25 |
| 6,372,717 B1 | 4/2002 | Greff | |
| 6,620,419 B1 | 9/2003 | Lintner | |
| 6,974,799 B2 | 12/2005 | Lintner | |
| 7,354,926 B2 | 4/2008 | Lintner | |
| 2004/0120918 A1 | 6/2004 | Lintner et al. | |
| 2006/0165643 A1 | 7/2006 | Lintner | |
| 2008/0213198 A1 | 9/2008 | Lintner et al. | |
| 2009/0010976 A1 | 1/2009 | Lintner | |
| 2009/0017147 A1 | 1/2009 | Lintner et al. | |
| 2009/0029926 A1 | 1/2009 | Lintner | |
| 2009/0186826 A1 | 7/2009 | Lintner et al. | |
| 2009/0214607 A1 | 8/2009 | Lintner et al. | |
| 2009/0253666 A1 | 10/2009 | Lintner et al. | |
| 2009/0269395 A1 | 10/2009 | Lintner et al. | |

FOREIGN PATENT DOCUMENTS

| | | |
|---|---|---|
| FR | 1477048 A | 4/1967 |
| FR | 2091516 A5 | 1/1972 |
| FR | 2183612 A1 | 12/1973 |
| FR | 2315991 A1 | 1/1977 |
| FR | 2465780 A1 | 3/1981 |
| FR | 2482128 A1 | 11/1981 |
| GB | 1539625 A | 1/1979 |
| WO | 83/01571 A1 | 5/1983 |
| WO | 92/08685 A1 | 5/1992 |
| WO | WO-00/43417 A1 | 7/2000 |
| WO | WO-01/64178 A1 | 9/2001 |

OTHER PUBLICATIONS

Database WPI, Section Ch, Week 200064, Derwent Publications Ltd., London, GB: Class B05, AN 2000-658372 XP002216648 & JP 2000 219639 A (Toyo Yakuhin Kogo KK), Aug. 8, 2000.
Lubach et al., Br. J. Dermatol., 135 (1996) 733-737.
Brand and Braathen, Dermatology, 193 (1996) 283-288.
Yokoyama and Benoit, Am. J. Physiol., 270 (1996) G752-756.
D.E. Dobbins et al., Microcirc. Endothelium Lymphatics, 6 (1990) 409-425.
I. Sakieki, Nippon Kagaku Zasshi, 79 (1958) 733. (Only English translation of abstracts provided on pp. 733 & 736 in reference).
Kullmann et al., J. Biol. Chem., 255 (1980) 8234.

* cited by examiner

*Primary Examiner* — Hope A Robinson
(74) *Attorney, Agent, or Firm* — Lerner, David, Littenberg, Krumholz & Mentlik, LLP

(57) ABSTRACT

The invention relates to novel cosmetic or dermopharmaceutical compositions for topical use which are used to prevent the symptoms of cutaneous slackening and, more specifically, to treat the visible signs of ageing and fatigue, such as bags and circles under the eyes. The inventive compositions comprise, in a cosmetically-acceptable medium, a combination of at least two, and preferably three, components selected from: a) hesperidin or the derivatives thereof; b) A.C.E. enzyme inhibitor dipeptides; and c) oligopeptides $R_2$-$(AA)_n$-Pro-Arg, wherein $(AA)_n$ is a peptide chain, (AA) is any amino acid or any derivative of any amino acid, n is included between 1 and 3, and $R_2$=H or an alkoyl chain having a carbon length of between $C_2$ and $C_{22}$.

18 Claims, No Drawings

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Gly Gln Pro Arg
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitoyl-Gly

<400> SEQUENCE: 2

Gly Gln Pro Arg
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: H-Gly or alkoyl-Gly with an alkoyl chain of
      length 2 to 18 carbons

<400> SEQUENCE: 3

Gly Gln Pro Arg
1

<210> SEQ ID NO 4
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 4

Ala Gln Pro Arg
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: H-Gly or alkoyl-Gly with an alkoyl chain of
      length 2 to 22 carbons

<400> SEQUENCE: 5

Gly Gln Pro Arg
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: H-Ala or alkoyl-Ala with an alkoyl chain of
      length 2 to 22 carbons

<400> SEQUENCE: 6

Ala Gln Pro Arg
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: H-Gly

<400> SEQUENCE: 7

Gly Gln Pro Arg
1
```

COSMETIC OR DERMOPHARMACEUTICAL COMPOSITIONS WHICH ARE USED TO REDUCE BAGS AND CIRCLES UNDER THE EYES

SEQUENCE LISTING

The instant application contains a Sequence Listing which has been submitted via EFS-Web and is hereby incorporated by reference in its entirety. Said ASCII copy, created on May 27, 2010, is named SEDERM3.3-004MAY27 ST25.txt, and is 1,941 bytes in size.

TECHNICAL FIELD

The present invention relates to the field of cosmetics and dermopharmaceuticals.

BACKGROUND OF THE INVENTION

The present invention concerns new cosmetic or dermopharmaceutical compositions for topical use aimed at preventing the symptoms of skin slackening, and more particularly intended for the treatment of visible signs of ageing and fatigue, especially "bags" and "circles" under the eyes, which contain, in a cosmetically acceptable base, a combination of at least two, and preferably three, constituents chosen from among:
  a) hesperidin or hesperidin derivatives,
  b) dipeptides that inhibit the enzyme ACE (angiotensin converting enzyme EC 3.4.15.1), particularly ones chosen from those containing the sequence H-Val-Trp-$OR_1$, H-Val-Tyr-$OR_1$, H-His-Tyr-$OR_1$, H-Arg-Phe-$OR_1$, H-Tyr-Trp-$OR_1$, with $R_1$=H or a $C_1$ to $C_{24}$ alkyl chain, preferably either $C_1$ to $C_3$ or $C_{14}$ to $C_{18}$, or with $R_1$=$NR_2R_3$ where $R_2$ and $R_3$ independently of each other are H or an alkyl chain with 1 to 12 carbon atoms, preferably 1 to 3 carbon atoms, and
  c) oligopeptides $R_2$-$(AA)_n$-Pro-Arg OH where $(AA)_n$ is a peptide chain, (AA) being any amino acid or any derivative of any amino acid and "n" being between 1 and 3, while $R_2$=H or an alkoyl chain between 2 and 22 carbons in length.

Skin is the immediate outward characteristic that we present to the outside world, and its appearance has always been a subject of preoccupation.

Current knowledge of skin physiology now makes it possible to propose cosmetic solutions to a variety of dysfunctions induced by external aggressive agents or by ageing. Many aspects are nevertheless still unknown, poorly understood, and badly managed.

This is the case, for example, with the symptom commonly called "bags under the eyes" or "puffy eyes". This skin condition below the eyes, characterized by a degree of swelling, often irritation, flaccidity of the skin, and redness, does not have a clearly defined aetiology well described in the literature.

While in certain cases hypothyroidism is evoked, in others a connection is established between allergy leading to rhinitis and retention of water in parts of the face (nose, eyes, sinuses, and adjacent areas). Fatigue, excessive smoking, and the associated skin irritation phenomena also contribute to the appearance of "bags". A general examination of the literature on the subject reveals connections between inflammation, oedema, and water retention/sodium balance, disturbances in lymph drainage, and venous insufficiency combined with capillary fragility. Age and slackening of the cutaneous tissues, which are particularly thin around the eyes, also of course play a role.

Though it is often neglected, the quality of lymphatic circulation is one of the major factors allowing the skin to maintain its aesthetic and physiological characteristics (see, for example, Lubach et al., Br. J. Dermatol., 135 (1996) 733-737; Brand and Braathen, Dermatology, 196 (1996) 283-288). Within the organism, the lymphatic system has a variety of complex functions, which cover domains such as nutrition or immunology.

As far as this patent application is concerned, as a theoretical physiological approach, one may consider schematically that the lymphatic system is a drainage system, which regulates various physiological fluids, collecting the excess amounts of extracellular fluid and its contents to promote their return to the bloodstream (approximately 3 litres per day).

The system is made up of three distinct elements: capillaries situated in the extracellular spaces, lymph nodes and vessels.

The collection of extracellular fluids takes place in the capillaries. The capillary walls are made of mutually overlapping endothelial cells. Under the pressure of extracellular fluid, these overlapping cells tip slightly towards the interior, like revolving doors, which turn in only one direction. The fluid entering the capillary cannot go back. Subsequently a succession of valves along the lymphatic system prevents reflux of lymph back towards the capillaries. Lymph is a clear fluid, whose composition is close to that of blood with the exception of the red corpuscles, which transports lymphocytes, nutrients, hormones, and metabolites. Lymph is not pumped like blood, but circulates in the lymphatic system as a result of squeezing of the lymphatic vessels by the surrounding muscles. Via specific receptors, the regulation of lymph circulation is under the control of numerous neuromediators such as bradykinin, which act both on the frequency and on the intensity of contractions propelling lymph by peristaltic action within the lymphatic system. It is thus possible to correct dysfunctions (in frequency and/or intensity) in this lymph peristalsis by pharmacological measures (see, for example, Yokoyama and Benoit, Am. J. Physiol., 270 (1996) G752-756).

Many cosmetic compositions intended to improve the appearance of facial skin have now been proposed, including moisturizers, antiwrinkle creams, and irritation-soothing lotions. To our knowledge none of them has addressed the problem of "bags under the eyes" in a systematic and concerted manner, acting at several levels on both causes and symptoms at the same time.

The aim of the present invention is to resolve the aesthetic problem posed by these "bags" by acting simultaneously on water retention, inflammation, capillary fragility, and slackening of the cutaneous tissues by a synergistic combination of three active substance categories, namely hesperidins, peptide inhibitors of angiotensin I and angiotensin II converting enzyme, and immunomodulating peptides, immunoglobulin fragments.

Thus, in accordance with one of the objectives of the present invention, new cosmetic and dermopharmaceutical compositions are now proposed, in particular for the care of the skin of the face, which are essentially characterized in that they comprise, in a cosmetically acceptable base, at least two, and preferably three, active substances chosen from among:
  a) hesperidin or hesperidin derivatives,
  b) dipeptides that inhibit the enzyme ACE (angiotensin converting enzyme EC 3.4.15.1), particularly ones chosen from those containing the sequence H-Val-Trp-$OR_1$, H-Val-Tyr-$OR_1$, H-His-Tyr-$OR_1$, H-Arg-Phe-$OR_1$, H-Tyr-Trp-$OR_1$, with $R_1$=H or a $C_1$ to $C_{24}$ alkyl chain, preferably either $C_1$ to $C_3$ or $C_{14}$ to $C_{18}$, or with $R_1 = NR_2R_3$ where $R_2$ and $R_3$ independently of each other are H or an alkyl chain with 1 to 12 carbon atoms, preferably 1 to 3 carbon atoms, and c) oligopeptides $R_2$-$(AA)_n$-Pro-Arg 011 where $(AA)_n$ is a peptide chain, (AA) being any amino acid or any derivative of any amino acid and "n" being between 1 and 3, while $R_2 = H$ or an alkoyl chain between 2 and 22 carbons in length.

Another objective of the present invention is the use of such compositions as, or for the production of, cosmetic or dermopharmaceutical compositions intended for face care, and in particular for the treatment of bags and circles under the eyes.

Yet another objective of the present invention is a process of cosmetic treatment of the skin of the face, in particular of bags and circles under the eyes, which consists essentially of applying to the regions in question an effective amount of a composition in accordance with the invention. Certain other characteristics, aspects, and advantages of the present invention will emerge from the detailed description given below.

DETAILED DESCRIPTION

Hesperidin and its derivatives, and in particular hesperidin methyl chalcone, are substances that are natural or are modified synthetically starting from the natural substance, and are known for their vitamin P activity. French Patent 2 183 612 describes their use for the treatment of capillary fragility. Hesperidin methyl chalcone is currently used in pharmaceutical products as a vasodilator and capillary permeability modifier.

As has already been mentioned, lymph drainage is under the control of certain neuromediators, among them bradykinin, a circulating nonapeptide which stimulates lymph evacuation by activation of muscles surrounding the vascular network. The level of circulating bradykinin is modulated by an enzyme, known as angiotensin converting enzyme or ACE (EC 3.4.15.1), which rapidly degrades bradykinin. Certain dipeptides, among them the dipeptide Val-Trp, are known for their ability to inhibit this converting enzyme (D. E. Dobbins et al., Microcirc. Endothelium Lymphatics, 6 (1990) 409-425). They are therefore capable of improving lymph drainage by increasing lymph circulation, by regulating the levels of circulating bradykinin, thus exerting an effect on lymph peristalsis, whose final outcome is a skin from which noxious fluids and catabolites have been washed from the inside.

The use of these dipeptides, and in particular of Val-Trp, leads to another beneficial effect in this context. It has already been said that the appearance of "bags" is also connected with the phenomena of water retention and local oedema. It is known that the peptide angiotensin II (resulting from the conversion of angiotensin I by the above-mentioned enzyme ACE) is a powerful vasoconstrictor which increases at the same time both thirst and the phenomenon of general water retention in the vascular system. ACE inhibition by these dipeptides therefore decreases the circulating level of angiotensin II (the sole active form) while at the same time increasing the levels of bradykinin. The peptide Val-Trp thus acts against water retention, sodium imbalance (also implicated in the formation of "bags"), and local development of the associated oedemas.

The known angiotensin converting enzyme inhibitors cannot all be used in cosmetics, for a variety of reasons connected with tolerability to toxicity, legislation, compatibility with the formulations, or bioavailability. It is therefore evident that some chemical modifications (changing the hydrophilic character or lyophilization to improve solubility or skin penetration capacity) can be made to these compounds, while retaining their initial activity of inhibition of the converting enzyme.

In the particular case of dipeptide ACE inhibitors characterized by the structure H—X—Y—OH, in which X=Val, His, Trp, Arg, or Tyr and Y=Tyr, Phe, or Trp, it is possible to esterify the carboxyl group with an alcohol, straight-chain or branched, hydroxylated or not, leading to the formation of compounds H—X—Y—$OR_1$, possibly by amidation with an amine leading to compounds H-Val-Trp-$ONR_2R_3$, where $R_1$=a $C_1$ to $C_{24}$ alkyl chain, preferably $C_1$ to $C_3$ or $C_{14}$ to $C_{18}$, and with $R_2$ and $R_3$ independently of each other being H or an alkyl chain with 1 to 12 carbon atoms, preferably 1 to 3 carbon atoms, without these modifications changing in any way the activity of these compounds on the converting enzyme.

In the third place, the peptide Gly-Gln-Pro-Arg (SEQ ID NO:1) and its derivatives are known (PCT/FR00/00031) for their antiinflammatory activity, and in particular for their ability to inhibit secretion of interleukin 6 (IL-6) in skin cells. In the course of the studies leading to the present invention it was discovered that this peptide, and in particular its derivative form palmitoyl-Gly-Gln-Pro-Arg (SEQ ID NO:2), has certain unsuspected cosmetic properties, namely a firming and restructuring effect on the skin of the face and neck. Through this restructuring action it also contributes to better hydration of the skin covering.

The object of the present invention is thus the discovery that the cosmetic use, by topical application, of a combination of at least two, and preferably three, compounds of the complementary action described, namely:

a) hesperidin or hesperidin derivatives, b) dipeptides that inhibit the enzyme ACE (angiotensin converting enzyme EC 3.4.15.1), particularly ones chosen from those containing the sequence H-Val-Trp-$OR_1$, H-Val-Tyr-$OR_1$, H-His-Tyr-$OR_1$, H-Arg-Phe-$OR_1$, H-Tyr-Trp-$OR_1$, with $R_1$=H or a $C_1$ to $C_{24}$ alkyl chain, preferably either $C_1$ to $C_3$ or $C_{14}$ to $C_{18}$, or with $R_1 = NR_2R_3$ where $R_2$ and $R_3$ independently of each other are H or an alkyl chain with 1 to 12 carbon atoms, preferably 1 to 3 carbon atoms, and c) oligopeptides $R_2$-$(AA)_n$-Pro-Arg OH where $(AA)_n$ is a peptide chain, (AA) being any amino acid or any derivative of any amino acid and "n" being between 1 and 3, while $R_2 = H$ or an alkoyl chain between 2 and 22 carbons in length, makes it possible to achieve a significant reduction of "bags and/or circles under the eyes". For this purpose it is enough to incorporate the active compounds in sufficient and effective concentrations in acceptable cosmetic or dermopharmaceutical compositions and to apply a sufficient and effective quantity on the parts of the face in question, over a period of time ranging from 2 weeks to 2 months or longer.

Hesperidin or its derivatives may be obtained by extraction from a number of plants (Citrus spp., Ruscus spp., and others). A form particularly preferred for the realization of this invention is hesperidin methyl chalcone, also called trimethylhesperidin chalcone. This is usually obtained by alkylation of natural hesperidin using dimethyl sulfate in an alkaline medium (I. Sakieki, Nippon Kagaku Zasshi, 79 (1958) 733), but other methods can also be used by those skilled in the art. Other alkyl derivatives of natural or synthetic hesperidin are also included in the present application.

The hesperidin or its derivatives are used in the cosmetic compositions in accordance with the invention in concentrations varying between 0.001% (w/w) and 50% (w/w), preferably between 0.01% (w/w) and 10% (w/w), and more particularly between 0.05% (w/w) and 1% (w/w).

The dipeptide ACE inhibitors H—X—Y—OH with X=Val, His, Trp, Arg, or Tyr and Y=Tyr, Phe, or Trp can be obtained by classic chemical syntheses (in homogeneous or heterogeneous phase) or by enzymatic synthesis (Kullmann et al., J. Biol. Chem., 255 (1980) 8234) starting from the constituent amino acids or from their derivatives.

To improve the bioavailability of these dipeptides and their passage through skin, one can increase their lipophilic character by esterification of the carboxyl group with an alcohol, straight-chain or branched, hydroxylated or not, leading to the formation of compounds H—X—Y—$OR_1$, possibly by amidation with an amine leading to compounds H—X—Y—$ONR_2R_3$ where $R_1$=a $C_1$ to $C_{24}$ alkyl chain, preferably $C_1$ to $C_3$ or $C_{14}$ to $C_{18}$, and with $R_2$ and $R_3$ independently of each other being H or an alkyl chain with 1-12 carbon atoms and preferably 1-3 carbon atoms.

The dipeptides can equally be obtained by fermentation of a bacterial strain, modified or not by genetic engineering, to obtain the desired sequences or their various fragments.

Finally, the dipeptides can be obtained by extraction from proteins of animal or plant origin, preferably plant origin (for example from wheat or rice, in which their presence has been demonstrated—Saito, 1993), which may contain these sequences within their structure, followed by a controlled hydrolysis, enzymatic or non-enzymatic, which liberates the peptide fragment of the Val-Trp sequence in plants that may contain these sequences within their structure. Controlled hydrolysis allows the separation of these peptide fragments.

For the realization of the invention it is possible, but not necessary, to either extract the proteins relevant first and then to hydrolyse them, or to carry out the hydrolysis first on a crude extract and subsequently to purify the peptide fragments. It is also possible to use the hydrolysate without extracting the peptide fragments in question, making sure, however, that the enzymatic hydrolysis reaction has been arrested in time and confirming the presence of the peptides in question by appropriate analytical methods (radioactivity tracing, immunofluorescence, immunoprecipitation with specific antibodies, etc.).

Other simpler or more complex processes, leading to these products at lower cost or yielding higher purity, will be easily envisaged by those skilled in the art and familiar with the extraction and purification of proteins and peptides.

The peptide ACE inhibitors and their derivatives described above are used in the cosmetic compositions in accordance with the invention in concentrations that may vary between 0.0001% (w/w) and 1% (w/w), and preferably between 0.001% (w/w) and 0.05% (w/w).

The third constituent of the invention consists of one or more peptides with the sequence R2-(AA)n-Pro-Arg, where (AA)n is a peptide chain in which (AA) represents any amino acid or any derivative of any amino acid and n is between 1 and 3, while R2=H or an alkoyl chain with a length of 2 to 22 carbon atoms. The chain (AA)n is preferably glycyl-glutaminyl (H-Gly-Gln-O—) and R2 is preferably an alkoyl chain with a length of between 2 and 22 carbon atoms, and in particular the palmitoyl chain (C16).

These peptides are used in the cosmetic compositions in accordance with the invention in concentrations that may vary between 0.0001% (w/w) and 1% (w/w), and preferably between 0.001% (w/w) and 0.05% (w/w).

According to one embodiment of the invention, the cosmetic compositions contain hesperidin methyl chalcone in concentrations between 0.05 and 1.0% (w/w), the synthetic peptide H-Val-Trp-OR1 with R1=H or CH3 or —NH2 in concentrations varying between 0.001 and 0.01% (w/w), and the peptide R2-Gly-Gln-Pro-Arg (SEQ ID NO:3) with R2=H or an alkoyl chain with a length of between 2 and 18 carbon atoms.

The compositions are, for example, emollient lotions, milks, or creams; milks and creams for care of skin or the hair; make-up-removing cleansing creams, lotions, or milks; foundation tint bases; sun-screen lotions, milks, or creams; artificial suntan lotions, milks, or creams; shaving creams and foams; aftershave lotions; shampoos, lip rouges, mascaras, or nail varnishes.

These compositions can also be presented in the form of lipsticks intended to apply colour or to protect the lips from cracking, or of make-up products for the eyes or tints and tint bases for the face.

When the compositions according to the invention are presented in the form of water-in-oil or oil-in-water emulsions, the fatty phase consists essentially of a mixture of fatty substances obtained by extraction or synthesis, with at least one oil and possibly another fatty substance. The fatty phase of the emulsions may constitute 5 to 60% of the total weight of the emulsion.

The aqueous phase of the said emulsions constitutes preferably 30 to 85% of the total weight of the emulsion. The proportion of the emulsifying agent may be between 1 and 20%, and preferably between 2 and 12% of the total emulsion weight. When the compositions according to the invention are presented in the form of oily, oleo-alcoholic, or aqueous-alcoholic lotions they may constitute, for example, sun-screen lotions containing a filter absorbing UV radiation or softening lotions for skin; the oily lotions may in addition constitute foam oils containing oil-soluble surfactant, bath oils, etc.

Among the principal adjuvants that may be present in compositions according to the invention one may cite organic or aqueous-glycolic solvents, including MP-diol and polyglycerols, fatty substances obtained by extraction or synthesis, ionic or non-ionic thickeners, softeners, opacifiers, stabilizers, emollients, silicones, α- or β-hydroxy acids, antifoaming agents, moisturizing agents, vitamins, perfumes, preservatives, sequestrating agents, colouring agents, gel-forming and viscosity-increasing polymers, surfactants and emulsifiers, other water- or fat-soluble active principles, plant extracts, tissue extracts, marine extracts, sun filters, and antioxidants.

The more particularly preferred mono- or poly-alcohols are chosen from among ethanol, isopropanol, propylene glycol, glycerol, and sorbitol.

As the fatty substance, among mineral oils one may cite liquid petrolatum; among animal oils whale oil, shark oil, seal oil, menhaden oil, halibut liver oil, cod liver oil, tunny-fish oil, turtle oil, neat's foot oil, horse foot oil, sheep's foot oil, mink oil, otter oil, marmot oil, etc.; and among vegetable oils almond oil, wheat germ oil, jojoba oil, sesame oil, sunflower seed oil, palm oil, walnut oil, karite nut oil, shorea oil, macadamia nut oil, blackcurrant seed oil, and the like.

Among the fatty acid esters one may use esters of C12 to C22 acids, saturated or unsaturated, and lower alcohols such as isopropanol or glycerol or aliphatic C8 to $C_{2-2}$ alcohols, straight-chain or branched, saturated or unsaturated, or C10-$C_{2-2}$ alkane 1,2-diols.

As the fatty substance one may also cite vaseline, paraffin, lanolin, hydrogenated lanolin, tallow, acetylated lanolin, and silicone oils.

Among waxes one may cite Sipol wax, lanolin wax, beeswax, Candelilla wax, monocrystalline wax, Carnauba wax, spermaceti, cocoa butter, karité nut butter, silicone waxes, hydrogenated oils solidified at 25° C., sucroglycerides, oleates, myristates, linoleates, and stearates of calcium, magnesium, and aluminium.

Among the aliphatic alcohols one may cite lauryl alcohol, cetyl alcohol, myristyl alcohol, stearyl alcohol, palmityl alcohol, oleyl alcohol, and Guerbet's alcohols such as 2-decyltetradecanol or 2-hexyldecanol. As emulsifying agents among the aliphatic polyoxyethylenated alcohols one may cite lauryl, cetyl, stearyl, and oleyl alcohols containing 2 to 20 moles of ethylene oxide, and among the glycerol alkoyl ethers C12-C18 alcohols containing 2-10 moles of glycerol. It may also be useful to include thickeners such as cellulose derivatives, polyacrylic acid derivatives, guar gum, carouba gum, or xanthan gum.

The composition according to the invention can also contain adjuvants commonly used in cosmetics and in dermatology, and in particular moisturizing agents, softeners, products for the treatment of skin conditions, sun filters, germicides, colouring agents, preservatives, perfumes, and propellants.

When the compositions according to the invention are in the form of dispersions, these may be dispersions of lecithin in water in the presence of a surfactant or they may be aqueous dispersions of lipid spherules consisting of organized molecular layers enclosing an encapsulated aqueous phase. The lipid compounds may be long-chain alcohols and diols, sterols such as cholesterol, phospholipids, cholesteryl sulfate and phosphate, long-chain amines and their quaternary ammonium derivatives, dihydroxyalkylamines, polyoxyethylenated aliphatic amines, long-chain amino alcohol esters, their salts and quaternary ammonium derivatives, phosphate esters of aliphatic alcohols such as hydrogen dicetyl phosphate or its sodium salt, alkyl sulfates such as sodium cetyl sulfate, fatty acids in the form of salts, or else lipids of the type of those described in French Patents Nos. 2 315 991, 1 477 048, and 2 091 516 or in international patent applications WO 83/01571 and WO 92/08685.

As other lipids one may use, for example, lipids containing a lipophilic long chain of 12 to 30 carbon atoms, saturated or unsaturated, branched or straight-chain, for example an oleyl, lanolyl, tetradecyl, hexadecyl, isostearyl, lauryl, or alkoylphenyl chain. The hydrophilic group in these lipids may be ionic or non-ionic. The non-ionic groups may be groups derived from polyethylene glycol. One can also use advantageously, as lipids forming the lamellar phase, polyglycol ethers such as those described in French Patents Nos. 1 477 048, 2 091 516, 2 465 780, and 2 482 128.

The ionic group may advantageously be a group derived from an amphoteric, anionic, or cationic compound.

Some other lipids described in international patent application WO 83/01571 as suitable for the formation of vesicles are glycolipids such as lactosylceramide, galactocerebroside, gangliosides and trihexosylceramide, as well as phospholipids such as phosphatidylglycerol and phosphatidylinositol.

The active substances may be substances of nutritional or pharmaceutical interest or ones having a cosmetic activity. When they are water-soluble they may be dissolved to produce a homogeneous solution or they are in the aqueous phase encapsulated within the vesicles. The water-soluble substances having a cosmetic and/or pharmaceutical activity may be products intended for skin and hair care or treatment, such as for example moisturizers such as glycerol, sorbitol, pentaerythritol, pyrrolidine acid and its salts; artificial suntan agents such as dihydroxyacetone, erythrulose, glyceraldehyde, γ-dialdehydes such as tartaric aldehyde, these products being possibly associated with colouring agents; water-soluble sun filters; antiperspirants, deodorants, astringents, fresheners, tonics, cicatrizants, keratolytics, depilatories, scents; plant tissue extracts such as polysaccharides; water-soluble colorants; anti-dandruff agents; antiseborrhoeic agents, oxidants such as bleaching agents, for example hydrogen peroxide; and reducing agents such as thioglycolic acid and its salts.

Mention can also be made of vitamins, hormones, enzymes such as superoxide dismutase, vaccines, antiinflammatories such as hydrocortisone, antibiotics, bactericidal agents, cytotoxic agents, or antitumour agents.

When the active substances are oil-soluble they may be incorporated in the walls of the vesicles. They may be chosen from the group formed by oil-soluble sun filters, substances intended for improving of the condition of dry or old skin, tocopherols, vitamins E, F, or A or their esters, retinoic acid, antioxidants, essential fatty acids, glycyrrhetinic acid, keratolytics, and carotenoids.

The three constituents a) to c) of the present invention (hesperidins, ACE inhibitor peptides, and H-(AA)n-Pro-Arg) can be used in cosmetic compositions in accordance with the invention either as individual additions or as a premix in a suitable excipient, and be in the form of solution, dispersion, emulsion, paste, or powder. They may be included individually or together in vehicles consisting of cosmetic carriers such as macro-, micro-, or nanocapsules, liposomes or chylomicrons, macro-, micro-, or nanoparticles or microsponges. They may also be adsorbed on organic polymer powders, talcs, bentonites, or other inorganic supports.

They may be used in any form whatsoever, or in a form bound to or incorporated in or absorbed in or adsorbed on macro-, micro-, and nanoparticles, or macro-, micro-, and nanocapsules, for the treatment of textiles, natural or synthetic fibres, wools, and any materials that may be used for clothing or for day or night underwear intended to come into contact with the skin, such as tights, underclothes, handkerchiefs, or cloths, to exert their cosmetic effect via this skin/textile contact and to permit continuous topical delivery.

Some representative but not limiting formulations are given below to illustrate the invention.

Example 1

Gel

|  | g/100 g |
| --- | --- |
| Carbomer | 0.3 |
| Propylene glycol | 2.0 |
| Glycerol | 1.0 |
| White petrolataum | 1.5 |
| Cylomethicone | 6.0 |
| Crodacol C90 | 0.5 |
| Lubrajel ® MS | 10 |
| Triethanolamine | 0.3 |
| H-Val-Trp-OH | 0.005 |
| Hesperidin methyl chalcone | 0.250 |
| Palmitoyl-Gly-Gln-Pro-Arg (SEQ ID NO: 2) | 0.0015 |
| Water, preservatives, perfume_qsp | 100 g |

This gel, prepared extemporaneously, may be used for daily application on the face, especially around the eyes, to reduce oedematous infiltrations.

Example 2

Cream

|  | g/100 g |
|---|---|
| Volpo S2 | 2.4 |
| Volpo S20 | 2.6 |
| Prostearyl 15 | 8.0 |
| Beeswax | 0.5 |
| Stearoxydimethicone | 3.0 |
| Propylene glycol | 3.0 |
| Carbomer | 0.25 |
| Triethanolamine | 0.25 |
| H-Val-Trp-OEt | 0.01 |
| Hesperidin | 0.050 |
| Ala-Gln-Pro-Arg (SEQ ID NO: 4) | 0.0005 |
| Water, preservatives, perfumes_qsp | 100 g |

This emulsion is used to moisturize, restructure, and soothe facial skin, particularly in the fragile skin zones.

The activities described at the beginning of this application are illustrated by the following examples.

Example 3

Ace-Inhibition Activity of the Dipeptide Val-Trp

The test is derived from Sigma Diagnostics method No. 305-UV.

Converting enzyme (EC 3.4.15.1) decomposes synthetic tripeptide FAPGG into FAP+glycylglycine. The change in optical density ($\Delta$OD) at 340 nm is directly proportional to disappearance of the FAPGG, which allows a quantification of the converting enzyme activity.

The inhibiting effect of a compound is investigated according to the same principle, but in the presence of various concentrations of the test compounds.

The table below shows the results (means and standard deviations) obtained in five different tests.

| Peptide tested | Concentration | $\Delta$OD | Standard deviation | Inhibition |
|---|---|---|---|---|
| None | — | 0.110 | 0.008 | |
| H-Val-Trp | 10 ppm | 0.080 | 0.010 | 27.3% |
| N-Palmitoyl-Val-Trp | 10 ppm | 0.112 | 0.012 | 0% |
| H-Val-Trp-OMe | 10 ppm | 0.076 | 0.013 | 30.9% |
| H-Val-Trp | 50 ppm | 0.018 | 0.008 | 83.4% |
| N-Palmitoyl-Val-Trp | 50 ppm | 0.0107 | 0.009 | 2.7% |
| H-Val-Trp-OMe | 50 ppm | 0.0106 | 0.010 | 90.2% |

These results demonstrate the inhibitory activity of the peptide, the loss of this activity when its chemical structure in the N-terminal part is modified, and its maintained activity after esterification.

Example 4

Antiinflammatory Activity of Peptide Palmitoyl-Gly-Gln-Pro-Arg (Pal-GQPR (SEQ ID NO:2)): regulation of the level OF IL-6

Normal human keratinocytes and fibroblasts are cultured in a conventional medium in the presence or absence of various concentrations (10-45 ppm) of peptide Pal-GQPR (SEQ ID NO:2). After 24 hours the cells are rinsed in the same medium without Pal-GQPR (SEQ ID NO:2) and, after being subjected to irradiation of 35 mJ/cm$^2$, the same cells are returned to the culture for 48 hours, without Pal-GQPR (SEQ ID NO:2) or in its presence in the same concentrations as during the initial culture period. Cellular IL-6 is then determined using a standard ELISA test kit.

The two tables below show the results obtained in five different experiments carried out with the peptide specified at the top of the table, the results (means, $\sigma$) being expressed in pg/ml/20 000 cells.

TABLE 1

| N-Palmitoyl-Gly-Gln-Pro-Arg (SEQ ID NO: 2) (ppm) | | | | | | |
|---|---|---|---|---|---|---|
| | | 0 | 10 | 15 | 30 | 45 |
| Fibroblasts | Not irradiated | 23.1 ± 5.0 | 22.2 ± 3.8 | 18.4 ± 2.5 | 18.0 ± 0.2 | 17.0 ± 2.2 |
| | Irradiated | 108.1 ± 25.0 | 94.7 ± 11.2 | 75.5 ± 3.2 | 71.8 ± 10.0 | 56.2 ± 8.0 |
| Keratinocytes | Not irradiated | 0.071 ± 0.01 | 0.055 ± 0.01 | 0.053 ± 0.01 | 0.038 ± 0.01 | 0.036 ± 0.01 |
| | Irradiated | 0.752 ± 0.01 | 0.519 ± 0.15 | 0.490 ± 0.24 | 0.376 ± 0.09 | 0.325 ± 0.05 |

Under "control" conditions (absence of peptide in the course of the experiment) the literature data are thus confirmed as regards the overproduction of IL-6 by cells exposed to UV, since increases in the baseline level are observed both for fibroblasts and for keratinocytes, of respectively 368% (108.1 vs. 23.1) and 959% (0.752 vs. 0.071).

On the basis of these data it is evident that the peptide Pal-GQPR (SEQ ID NO:2) has two important effects on the two cell types tested:

Reduction of the baseline level of IL-6: All concentrations tested reduced the baseline level of IL-6 with, for example, maximum effect for the highest concentration tested, equal to 26.4% for fibroblasts and 49.2% for keratinocytes.

Reduction of the overproduction of IL-6 due to UV irradiation: All concentrations tested reduced the level observed in untreated cells, for example with a maximum effect for the highest concentration tested, equal to 48.0% for fibroblasts and 56.8% for keratinocytes.

Finally, it is important to note that the effects described above are strictly dependent on the product concentration used, which confirms the specificity of action of the peptide.

In parallel with this, to make certain that the concentration reductions observed were not due to cell mortality induced by the peptide itself, viability of the cells was verified by the conventional MTT test. The results demonstrated that, at the maximum concentration used (45 ppm), the test peptide does not exert any cytotoxic effect on the system studied.

Results of the same kind were obtained with other sequences tested under the same conditions.

Example 5

Effect on Bags Under the Eyes 21 persons (average age 51 years) took part in a test of a cream containing the three active constituents forming the object of this application:

The following formula was tested:

| Constituent | % (w/w) |
|---|---|
| Water | qsp 100 |
| Carbomer Ultrez 10 | 0.20 |
| Glycerol | 5.00 |
| Hydroxypropyl cellulose | 0.20 |
| Permulen TR2 (Goodrich) | 0.20 |
| Crodamol CAP (Croda) | 6.00 |
| Polysorbate 20 | 0.50 |
| Hesperidin methyl chalcone | 0.15 |
| H-Val-Trp-OH | 0.003 |
| Palmitoyl-Gly-Gln-Pro-Arg (SEQ ID NO: 2) | 0.001 |
| Perfume, preservatives | qsp |

The "bags" under the eyes were evaluated on the basis of the subjects' self-assessment questionnaires and by the technique of interference fringe projection, which makes it possible to measure face surface variations with a precision of $1/100$ mm. The product was applied twice daily for 56 days to the regions concerned. Measurements were carried out on days 0 and 56. Summarizing, a measurable reduction of the "bags" was observed, which could reach 1 mm in depth. In addition to this, the majority of the test subjects confirmed a "bag reduction" effect in the self-assessment questionnaires.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A topical cosmetic composition comprising a combination of at least two constituents selected from the group consisting of:

a) hesperidin or hesperidin methyl chalcone,
 b) dipeptides that inhibit the enzyme ACE (angiotensin converting enzyme EC 3.4.15.1) selected from the group consisting of H-Val-Trp-$OR_1$, H-Val-Tyr-$OR_1$, H-His-Tyr-$OR_1$, H-Arg-Phe-$OR_1$ and H-Tyr-Trp-$OR_1$, wherein $R_1$=H or a $C_1$ to $C_{24}$ alkyl chain or $R_1$=$NR_2R_3$, where $R_2$ and $R_3$ independently of each other are H or an alkyl chain with 1 to 12 carbon atoms, and
 c) oligopeptides selected from the group consisting of $R_2$-Gly-Gln-Pro-Arg (SEQ ID NO:5) and $R_2$-Ala-Gln-Pro-Arg (SEQ ID NO:6), wherein $R_2$=H or an alkoyl chain between 2 and 22 carbons in length, in a cosmetically acceptable base.

2. The topical cosmetic composition of claim 1, wherein said dipeptide is H-Val-Trp-OH.

3. The topical cosmetic composition of claim 1, wherein said dipeptide is obtained by chemical synthesis, an enzymatic route, fermentation, or extraction from proteins of plant origin.

4. The topical cosmetic composition of claim 1, wherein the oligopeptide is H-Gly-Gln-Pro-Arg (SEQ ID NO:7) or palmitoyl-Gly-Gln-Pro-Arg (SEQ ID NO:2).

5. The topical cosmetic composition of claim 1, wherein said hesperidin or hesperidin methyl chalcone are used in concentrations between 0.001% (w/w) and 50% (w/w).

6. The topical cosmetic composition of claim 1, wherein said dipeptide is used in concentrations between 0.0001% (w/w) and 1% (w/w).

7. The topical cosmetic composition of claim 1, wherein said oligopeptide is used in concentrations between 0.0001% (w/w) and 1% (w/w).

8. The topical cosmetic composition of claim 1, wherein constituents a) to c) are used in the form of solution, dispersion, emulsion, paste, or powder, as individual additions or in the form of a premix, or are included as individual additions or as a premix in vehicles constituted by carriers.

9. The topical cosmetic composition of claim 1, wherein constituents a) to c) are used as individual additions or in the form of a premix in a pharmaceutical formulation.

10. The topical cosmetic composition of claim 1, wherein said cosmetic composition contains at least one additional constituent selected from the group consisting of organic or aqueous-glycolic solvents, fatty substances ionic or non-ionic thickeners, softeners, opacifiers, stabilizers, emollients, silicones, α-hydroxy acids, antifoaming agents, moisturizing agents, vitamins, perfumes, preservatives, sequestrating agents, colouring agents, gel-forming and viscosity-increasing polymers, surfactants and emulsifiers, other water- or fat-soluble active substances, plant extracts, tissue extracts, marine extracts, sun filters, or antioxidants.

11. The topical cosmetic composition of claim 8, wherein said vehicles constituted by carriers are macro-, micro-, or nanocapsules, liposomes or chylomicrons, macro-, micro-, or nanoparticles or microsponges, or are adsorbed on organic polymer powders, talcs, bentonites, or other inorganic supports.

12. The topical cosmetic composition of claim 9, wherein said pharmaceutical formulation is selected from the group consisting of emollient lotions, emollient milks, emollient creams; milks or creams for care of the skin or hair; make-up-removing cleansing creams, lotions or milks; foundation tint bases; sun-screen lotions, milks or creams; artificial suntan lotions, milks or creams; shaving creams and foams; aftershave lotions; shampoos; lip rouges; lipsticks; mascaras; and nail varnishes.

13. A method of reducing visible signs of aging comprising applying the composition of claim 1 to areas of human skin showing signs of aging, wherein said composition is applied at least once a per day for a time period sufficient to provide a reduction in the visible signs of aging of that portion of human skin, wherein said time period is at least 2 weeks.

14. A method of reducing visible signs of human skin slackening comprising applying the composition of claim 1 to areas of human skin showing signs of skin slackening, wherein said composition is applied at least once per day for a time period sufficient to provide a reduction in the visible signs of skin slackening of that portion of human skin, wherein said time period is at least 2 weeks.

15. A method of treating a condition of "bags" under the eyes of human facial skin comprising applying the composition of claim 1 to areas of human facial skin showing signs of "bags" under the eyes, wherein said composition is applied at least once per day for a time period sufficient to provide a reduction in the visible signs of "bags" under the eyes of that portion of human skin, wherein said time period is at least 2 weeks.

16. A method of reducing the visible signs of fatigue comprising applying the composition of claim 1 to areas of human skin showing signs of fatigue, wherein said composition is applied at least once per day for a time period sufficient to provide a reduction in the visible signs of fatigue of that portion of human skin, wherein said time period is at least 2 weeks.

17. A method of delivering the composition of claim 1 to human skin, comprising binding, incorporating, or absorbing said composition in or on, macro-, micro- or nanoparticles, or macro-, micro- or nanocapsules, in textiles, natural or synthetic fibres, wools, or all materials used for clothing; and topically delivering said composition from said textiles, natural or synthetic fibres, wools, or all material used for clothing through direct contact with skin or with hair.

18. The topical composition of claim 1, wherein constituent a) is hesperidin methyl chalcone, constituent b) is H-Val-Trp-OH and constituent c) is palmitoyl-Gly-Gln-Pro-Arg (SEQ ID NO:2).

* * * * *

UNITED STATES PATENT AND TRADEMARK OFFICE
CERTIFICATE OF CORRECTION

PATENT NO. : 7,998,493 B2  Page 1 of 1
APPLICATION NO. : 10/504643
DATED : August 16, 2011
INVENTOR(S) : Karl Lintner It is certified that error appears in the above-identified patent and that said Letters Patent is hereby corrected as shown below:

In the Specification

Column 1, line 38, "-Pro-Arg OH" should read -- -Pro-Arg--.

Column 3, line 4, "-Pro-Arg 011" should read -- -Pro-Arg--.

Column 4, line 40, "–Pro-Arg OH" should read -- -Pro Arg--.

Column 16, line 4, "at least once a per day" should read --at least once per day--.

Column 16, line 22, "A method of reducing the visible" should read --A method of reducing visible--.

Signed and Sealed this
Eleventh Day of March, 2014

Michelle K. Lee
*Deputy Director of the United States Patent and Trademark Office*